US00PP34868P2

(12) United States Plant Patent
Hardigan et al.

(10) Patent No.: US PP34,868 P2
(45) Date of Patent: Dec. 27, 2022

(54) BLACKBERRY PLANT NAMED 'ZODIAC'

(50) Latin Name: ***Rubus* subg. *Rubus* Watson**
Varietal Denomination: Zodiac

(71) Applicant: The United States of America, as represented by the Secretary of Agriculture, Washington, DC (US)

(72) Inventors: Michael A. Hardigan, Corvallis, OR (US); Chad E. Finn, Corvallis, OR (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 17/687,937

(22) Filed: Mar. 7, 2022

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./203, 204
CPC ..... A01H 5/0887
See application file for complete search history.

(56) References Cited

PUBLICATIONS https://oregon-berries.com/wp-content/uploads/2020/02/2019-20ORBCreports.pdf; Dec. 2019; 4 pages.*

* cited by examiner

*Primary Examiner* — Kent L Bell
(74) *Attorney, Agent, or Firm* — John Fado; Ariel Atkinson

(57) ABSTRACT

A new and distinct blackberry cultivar that originated from seed produced from a cross between the thornless maternal blackberry plant 'ORDS 2707-1' (unpatented) and the thornless paternal blackberry plant 'ORDS 2785-2' (unpatented)). This new blackberry cultivar can be distinguished by its high yields of small-to-medium sized, uniformly shaped, glossy, and distinctly conical berries that can be machine harvested with good firmness and quality for a trailing type of blackberry. The berries are well suited for processing, with an excellent flavor characterized by mild sweetness, and a good sugar/acid balance. The new and distinct blackberry variety has fruit that are borne on vigorous canes which combine two distinct sources of genetic thornlessness ('Austin Thornless', 'Lincoln Logan') from the respective female and male parent.

7 Drawing Sheets

Latin name of the genus and species of the plant claimed: 'ZODIAC' is a blackberry plant that is *Rubus* subg. *Rubus* Watson.

Variety denomination: The new blackberry plant claimed is of the variety denominated 'Zodiac' *Rubus* subg. *Rubus* Watson.

BACKGROUND OF THE NEW PLANT

The present invention relates to a new and distinct blackberry cultivar designated 'Zodiac' and botanically known as *Rubus* subg. *Rubus* Watson. This new thornless blackberry cultivar was discovered in Corvallis, Oreg. in July 2011, and is the result of a 2008 cross between the maternal blackberry plant 'ORUS 2707-1' (unpatented) and the paternal blackberry plant 'ORUS 2785-2' (unpatented). 'ORUS 2707-1' was a selection from a cross of the thorny trailing blackberry 'ORUS 1368-1' (unpatented) and thornless trailing blackberry 'NZ 9351-4' (unpatented). 'ORUS 2785-2' was a selection from a cross of the wild *Rubus ursinus* blackberry accession 'GP 4-21' (unpatented) and the thornless trailing blackberry 'Waldo' (unpatented). 'Zodiac' thornlessness is derived from a combination of the 'Lincoln Logan' (unpatented) source on its maternal side, and the 'Austin Thornless' (unpatented) source on its paternal side. The original seedling of the new cultivar was asexually propagated in Benton County, Oreg. The new cultivar was established in vitro from a cane cutting and microcuttings have been taken and rooted from this sort of culture. The cultivar was referred to as 'ORUS 4222-1' internally as an experimental designation prior to release. The present invention has been found to be stable and reproduce true to type through successive asexual propagations.

SUMMARY OF THE NEW PLANT

The following are the most outstanding and distinguishing characteristics of this new cultivar when grown under normal horticultural practices in Oregon. The new cultivar is thornless and possesses a trailing growth habit. The new cultivar ripens in the mid-season for a trailing type, one week later than 'Columbia Star' (U.S. Plant Pat. No. 25,532). The new cultivar has high plant vigor and favorable lateral fruiting architecture compared to current cultivar standards, with a plant vigor rating similar to 'Columbia Star' and higher than 'Black Diamond' (unpatented), and a higher fruit per-lateral count than 'Columbia Star' and on par with 'Black Diamond'. Thus, the new cultivar appears to favorably combine the greater vegetative vigor and lateral lengths of 'Columbia Star' with the higher number of fruits per-lateral of 'Black Diamond' in a single variety. The cultivar demonstrated higher average yields than 'Black Diamond' and 'Columbia Star' in a 2017-planted trial in Aurora, Oreg. from 2019-2020, and higher yields in a 2019-planted trial in 2021 at the same location. The new cultivar has medium-size berries which release easily and possess sufficient firmness, skin toughness, and abrasion resistance to be machine harvestable. The fruit possess a high gloss and uniformly conical shape that narrows toward the tip of the berry, lending a distinct appearance. The new cultivar's fruit possessed higher soluble solids and acidity than 'Black Diamond' and 'Columbia Star' based on samples measured in 2016 and have excellent flavor and texture when eaten fresh.

BRIEF DESCRIPTION OF THE PHOTOGRAPHS

This new blackberry plant is illustrated by the accompanying photographs that show the plants, ripening fruit morphology, and harvested fruit; the colors shown are as true as can be reasonably obtained by conventional photographic procedures.

Figure 1:
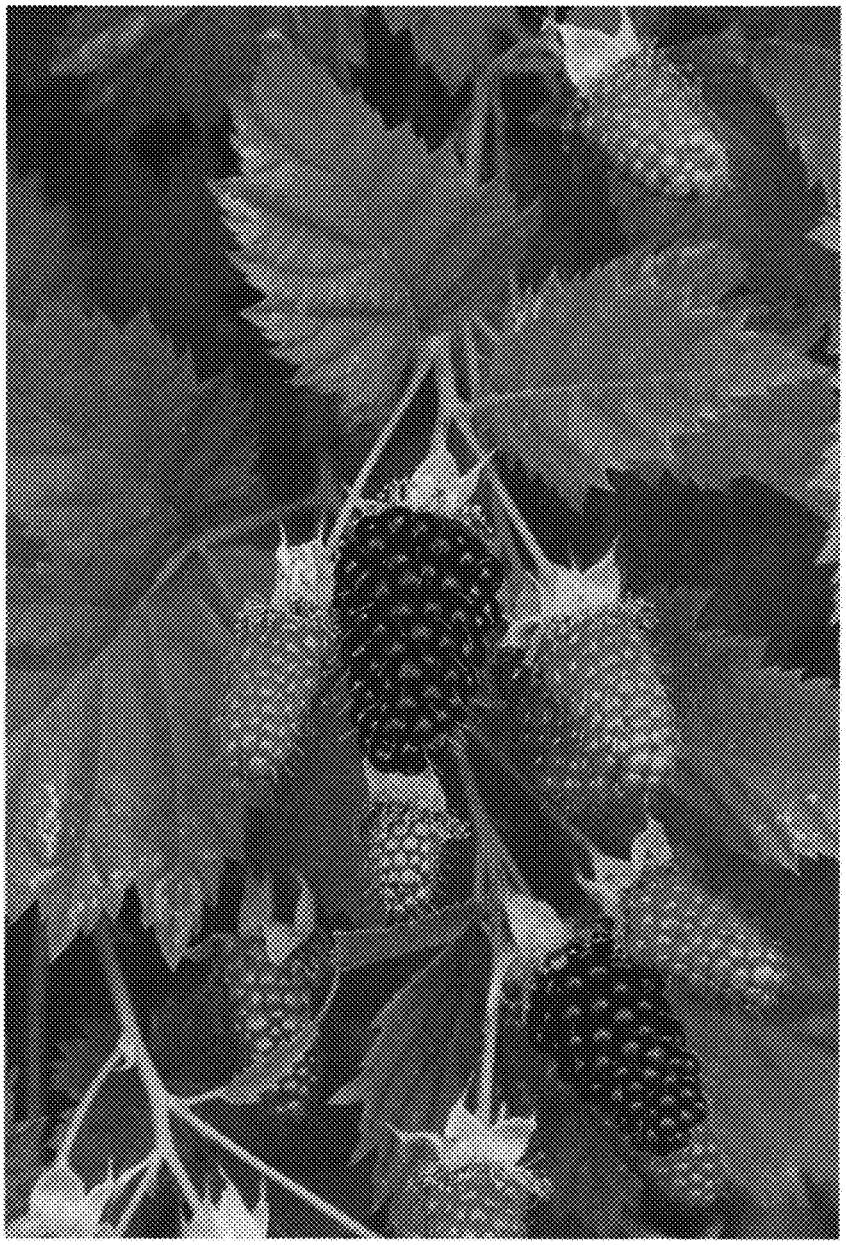
FIG. 1 shows an example of a fruiting cluster with ripe 'Zodiac' fruit.
Figure 2:
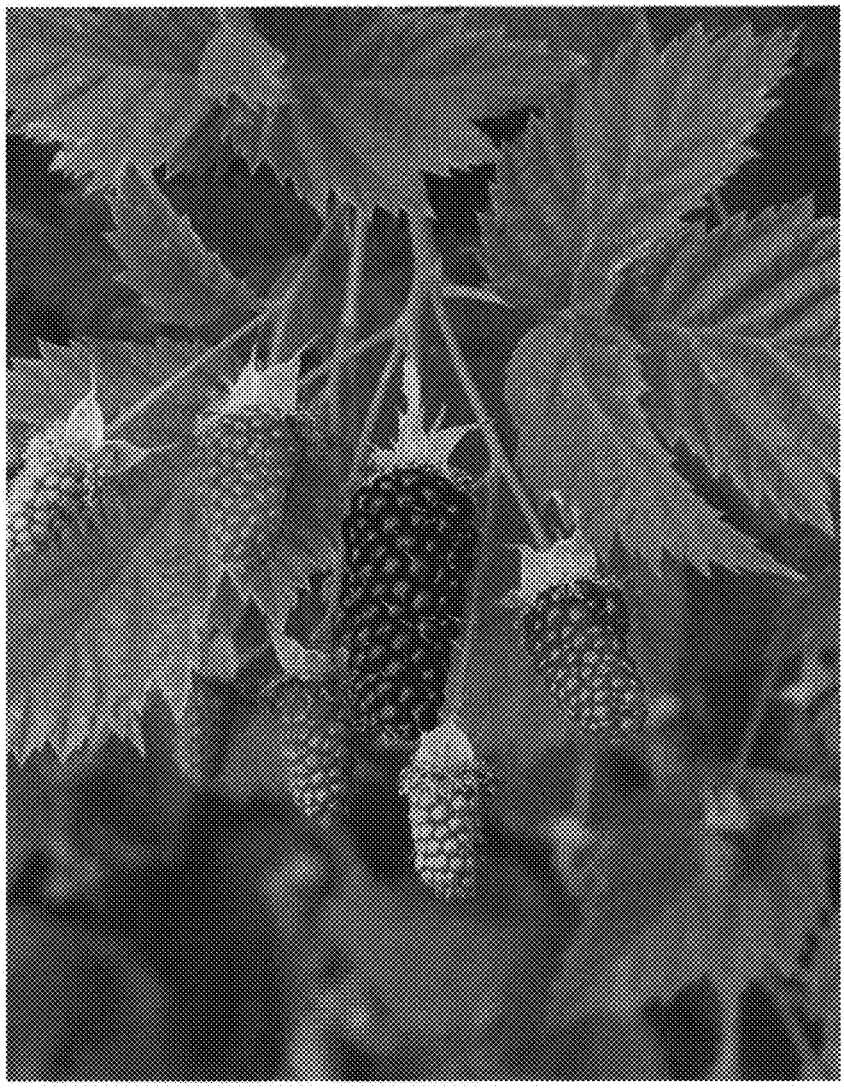
FIG. 2 shows an example of the conical shape of 'Zodiac' fruit which characterizes the distinct morphology of the cultivar.
Figure 3:
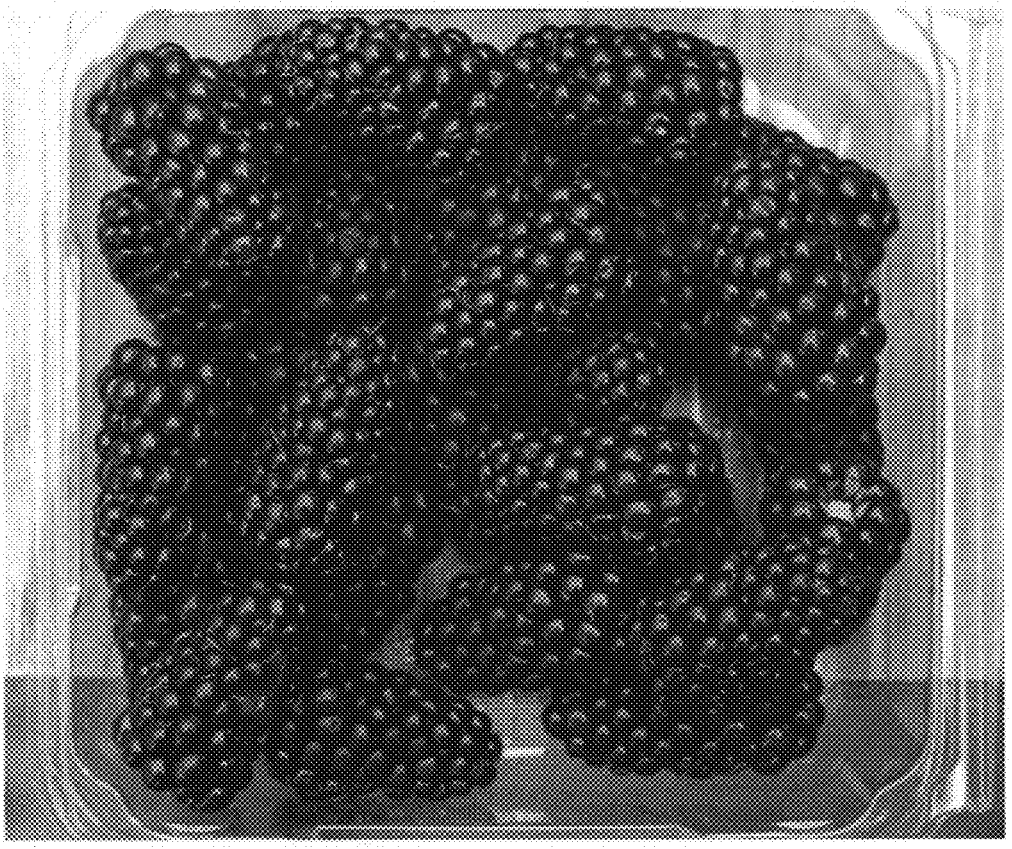
FIG. 3 shows a clamshell of 'Zodiac' fruit after 9 days of refrigerated storage at ~4° C.
Figure 4:
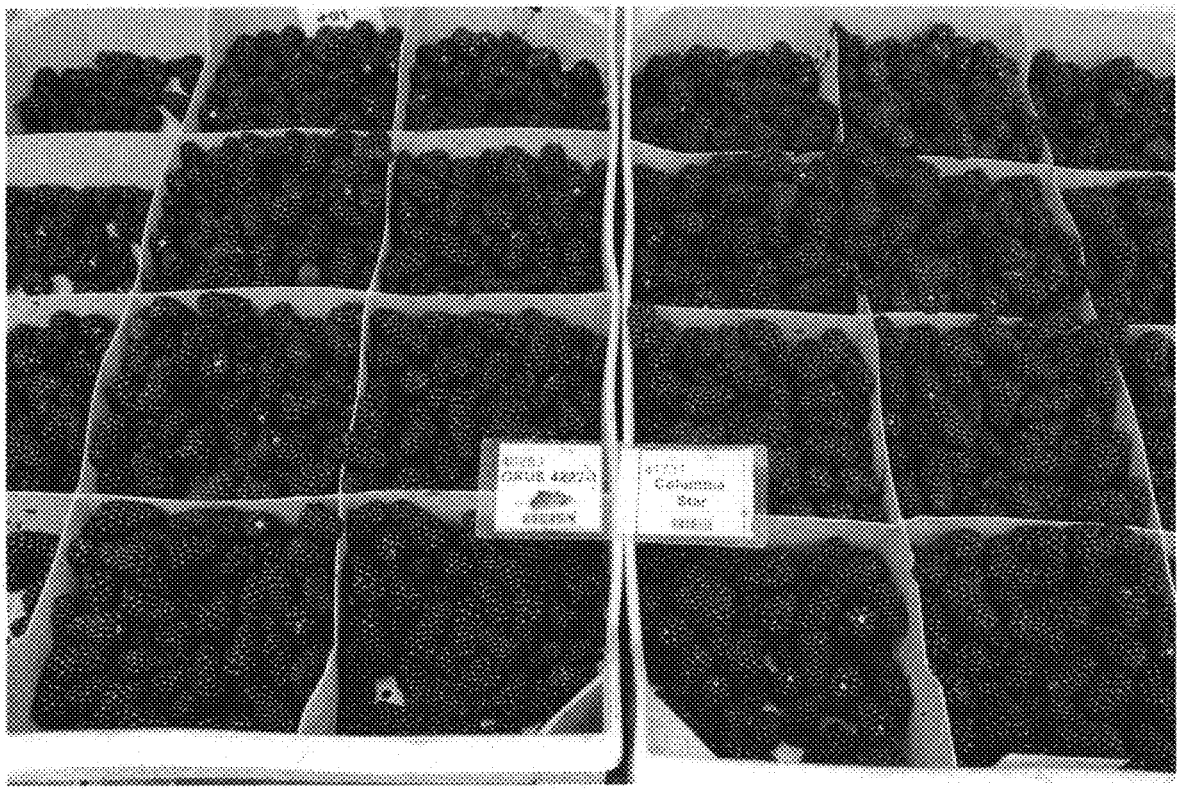

FIG. 4 shows a flat of harvested 'Zodiac' fruit (left) compared to a flat of 'Columbia Star' (U.S. Plant Pat. No. 25,532) fruit (right).

Figure 5:
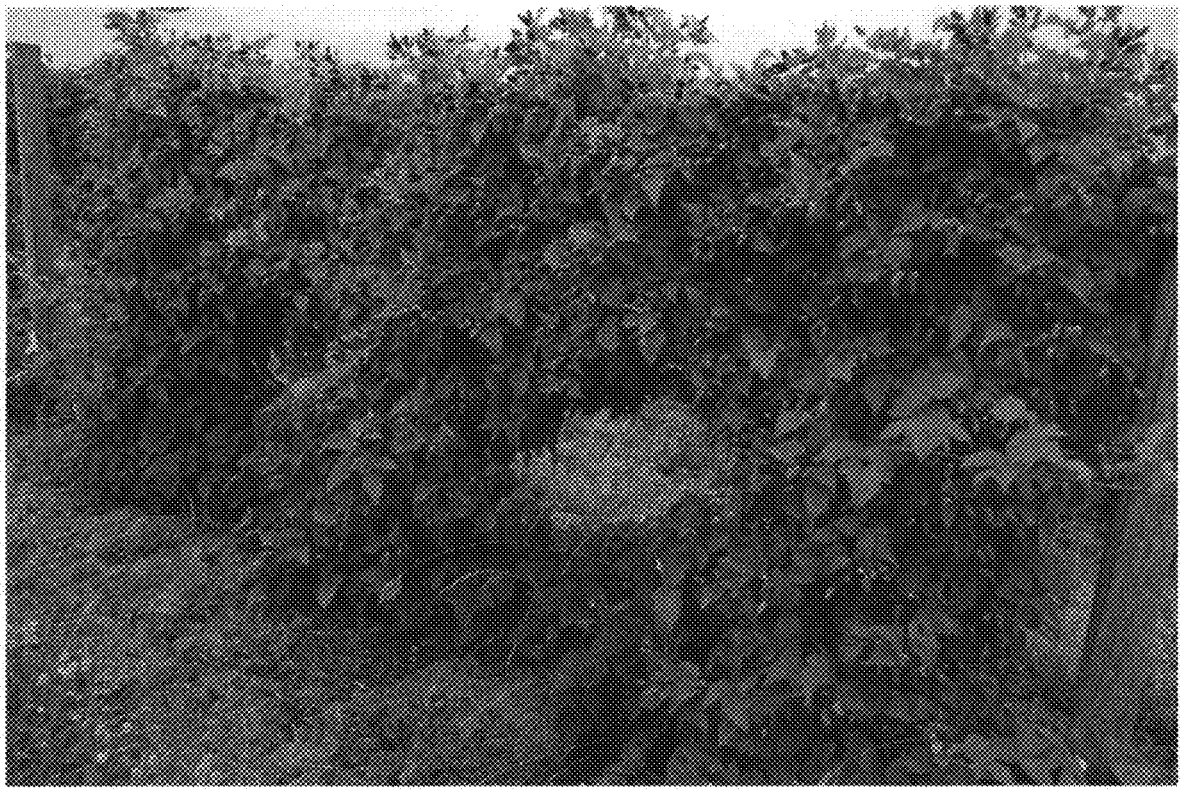

FIG. 5 shows a plot of entire 3 year old 'Zodiac' plants during ripening season in early July.

Figure 6:
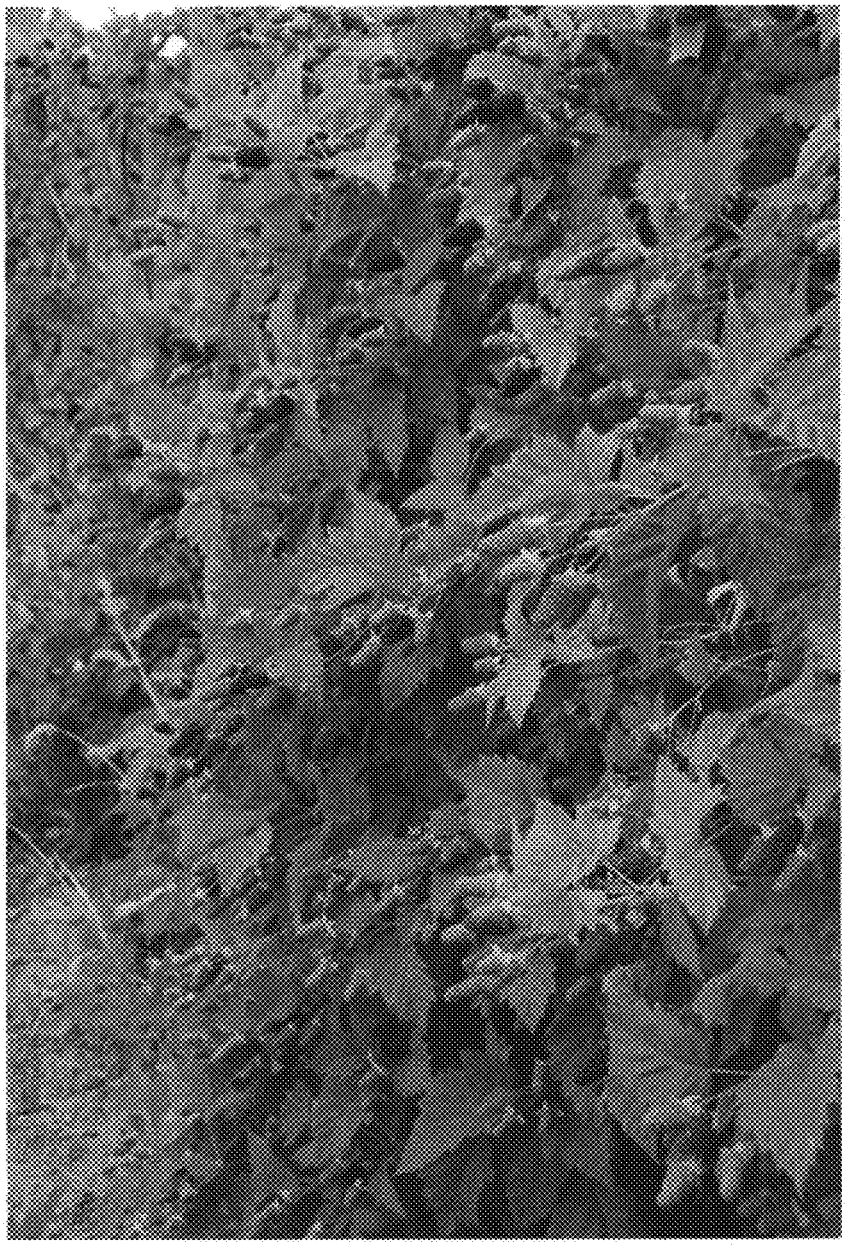

FIG. 6 shows the architecture and presentation of 'Zodiac' fruiting laterals protruding from the floricane canopy.

Figure 7:
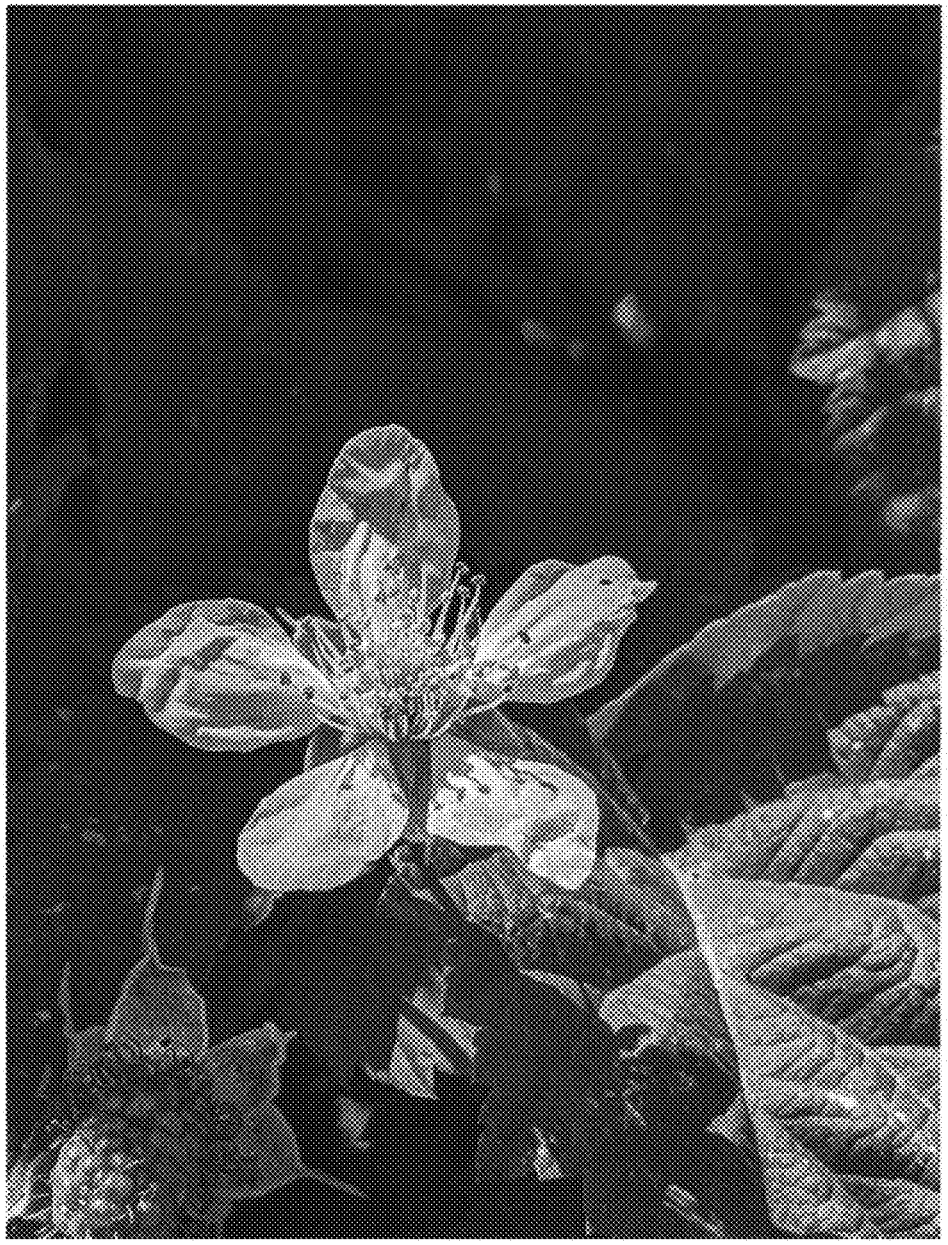

FIG. 7 shows the morphology of a 'Zodiac' flower.

DETAILED DESCRIPTION OF THE NEW CULTIVAR

The following description of 'Zodiac' is based on observations taken from 2012 to 2021 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic, and cultural conditions. 'Zodiac' has not been observed under all possible environmental conditions. Color terminology follows The Royal Horticultural Society Colour Chart London (R.H.S.) ($5^{th}$ edition, 2007).

Table 1 shows plant characteristics of the new cultivar compared with plant characteristics of the blackberry plants 'Columbia Star' and 'Black Diamond'. Characteristics include plant vigor, growth habit, date of bud-break, presence of spines further than 0.6 m from the soil surface, presence of spines less than 0.6 m from the soil surface, weight of primary fruit, uniformity of berry shape, fruit firmness, fruit flavor, fruit soluble solids (%; in Brix), fruit pH, fruit titratable acidity (% as citric acid), and yield (actual kg*plt-1). Fruit chemistry measurements are from 2017 trial data collected from Aurora, Oreg.

TABLE 1

| Characteristic | Zodiac | Columbia Star | Black Diamond |
|---|---|---|---|
| Plant vigor | High | High | Medium |
| Growth habit | Trailing | Trailing | Trailing |
| Date of budbreak | 27 Mar. 2012 | 27 Mar. 2012 | 27 Mar. 2012 |
| Presence of spines further than 0.6 m from the soil surface | Absent | Absent | Absent |
| Presence of spines less than 0.6 m from the soil surface | Absent | Absent | Numerous |
| Weight of primary fruit | 5.3 g | 7.7 g | 6.1 g |
| Uniformity of berry shape | Excellent | Excellent | Excellent |
| Fruit firmness | Very good | Very good | Good |
| Fruit flavor | Very good | Excellent | Good |
| Fruit soluble solids (%; in Brix) | 12.38 | 12.21 | 9.77 |
| Fruit pH | 3.32 | 3.25 | 3.31 |
| Fruit titratable acidity (% as citric acid) | 14.04 | 13.71 | 12.23 |
| Yield (actual kg · plt-1) | 7.90 | 7.54 | 7.01 |

Table 2 shows floricane and mature primocane characteristics of the new cultivar compared with floricane and mature primocane characteristics of the blackberry plants 'Columbia Star' and 'Black Diamond'. Characteristics include diameter at base, diameter at midpoint, diameter at terminus, internode length at base, internode length at midpoint, internode length at terminus, presence of spines further than 0.6 m from the soil surface, presence of spines less than 0.6 m from the soil surface, floricane color at base, floricane color at midpoint, floricane color at terminus, floricane lateral length, floricane lateral strength, primocane color at base, primocane color at midpoint, primocane color at terminus, and floricane length (range).

TABLE 2

| Characteristic | Zodiac | Columbia Star | Black Diamond |
|---|---|---|---|
| Diameter at base | 0.90 cm | 0.84 cm | 1.44 cm |
| Diameter at midpoint | 0.87 cm | 0.56 cm | 0.80 cm |
| Diameter at terminus | 0.46 cm | 0.31 cm | 0.55 cm |
| Internode length at base | 5.73 cm | 6.03 cm | 5.04 cm |
| Internode length at midpoint | 6.92 cm | 5.22 cm | 5.77 cm |
| Internode length at terminus | 3.98 cm | 3.81 cm | 4.90 cm |
| Presence of spines further than 0.6 m from the soil surface | Absent | Absent | Absent |
| Presence of spines less than 0.6 m from the soil surface | Absent | Absent | Numerous |
| Floticane color at base | RHS 143C | RHS 144A | RHS 152A |
| Floticane color at midpoint | RHS 143C | RHS 146C | RHS 152A |
| Floticane color at terminus | RHS 143C | RHS 144B | RHS 152B |
| Floticane lateral length | Medium-long | Medium-long | Short |
| Floticane lateral strength | Medium | Medium | Strong |
| Primocane color at base | RHS 143C | RHS 144A | RHS 144A w/red (187A) streaking |
| Primocane color at midpoint | RHS 143C | RHS 144A | RHS 146C w/red (187A) streaking |
| Primocane color at terminus | RHS 143C | RHS 144B | RHS 144A, often streaked w/red (187A) |
| Floticane length (range) | 3.1-6.4 m | 2.8-3.7 m | 2.7-4.3 m |

Table 3 shows primocane foliage characteristics of the new cultivar compared with primocane foliage characteristics of the blackberry plants 'Columbia Star' and 'Black Diamond'. Primocane characteristics include mature compound leaf width, mature compound leaf length, number of leaflets per primocane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, spine presence on leaves, pubescence on primocane leaflet: upper surface, pubescence on primocane leaflet: undersurface, primocane leaf color abaxial, primocane leaf color adaxial, petiole length, petiole color: upper surface, petiole color: undersurface, petiolule length: terminal leaflet, petiolule length: first distal leaflet, petiolule color: abaxial, petiolule color: adaxial, stipule length, and stipule width.

TABLE 3

| Characteristic | Zodiac | Columbia Star | Black Diamond |
|---|---|---|---|
| Mature compound leaf width | 22.80 cm | 22.07 cm | 19.75 cm |
| Mature compound leaf length | 22.82 cm | 22.42 cm | 18.83 cm |
| Number of leaflets per primocane compound leaf | Usually 6; ranges from 5-7 | Usually 5 | Usually 5; ranges from 3-7 |
| Mature leaflet shape | Ovate to Cordate | Ovate | Ovate to Cordate |
| Mature leaflet apex | Broadly acuminate | Acute | Broadly acuminate |
| Mature leaflet base | Cordate | Cordate | Round to cordate |
| Mature terminal leaflet width | 9.0 cm | 8.70 cm | 7.43 cm |
| Mature terminal leaflet length | 11.7 cm | 11.68 cm | 8.83 cm |
| Mature first lateral leaflet width | 6.0 cm | 4.92 cm | 7.72 cm |
| Mature first lateral leaflet length | 8.2 cm | 7.30 cm | 10.07 cm |
| Leaflet margin | Double serrate | Double serrate | Serrate |
| Leaflet serration teeth length | 0.45 cm | 0.42 cm | 0.24 cm |
| Leaflet serration teeth width at base | 0.63 cm | 1.07 cm | 0.40 cm |
| Spine presence on leaves | Absent | Absent | Very short, soft spines on sides and back of petiole, petiolules, midveins and larger lateral veins |
| Pubescence on primocane leaflet: upper surface | Light | Light | Sparse |
| Pubescence on primocane leaflet: undersurface | Medium | Light | Heavy, soft |
| Primocane leaf color abaxial | RHS 139A | RHS N137A | RHS N137 |
| Primocane leaf color adaxial | RHS 139A | RHS 137B | RHS 147B |
| Petiole length | 8.4 cm | 8.18 cm | 7.90 cm |
| Petiole color: upper surface | RHS 144C & 183B | RHS 144A | RHS 146A & 146B, maturing to 177A |
| Petiole color: undersurface | RHS 144C | RHS 144B streaked with red 184A | 1 RHS 44B |
| Petiolule length: terminal leaflet | 2.5 cm | 2.83 cm | 4.43 cm |
| Petiolule length: first distal leaflet | 0.5 cm | 0.28 cm | 0.68 cm |
| Petiolule color: abaxial | RHS 139A | RHS 200B | RHS 146A & 146B |
| Petiolule color: adaxial | RHS 139A | RHS 144B | RHS 144B |
| Stipule length | 1.45 cm | 2.20 cm | 0.90 cm |
| Stipule width | 0.27 cm | 0.20 cm | 0.23 cm |

Table 4 shows floricane foliage characteristics of the new cultivar compared with floricane foliage characteristics of the blackberry plants 'Columbia Star' and 'Black Diamond'. Floricane characteristics include mature compound leaf width, mature compound leaf length, number of leaflets per floricane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, pubescence on floricane leaflet: upper surface, pubescence on floricane leaflet: undersurface, floricane leaf color abaxial, floricane leaf color adaxial, petiole length, petiolule length: terminal leaflet, petiolule length: first distal leaflet, petiolule color: abaxial, petiolule color: adaxial, stipule length, and stipule width.

TABLE 4

| Characteristic | Zodiac | Columbia Star | Black Diamond |
|---|---|---|---|
| Mature compound leaf width | 14.4 cm | 16.70 cm | 11.57 cm |
| Mature compound leaf length | 13.8 cm | 16.07 cm | 11.68 cm |
| Number of leaflets per floricane compound leaf | Usually 3 | Usually 3 | Usually 3; occasionally 1 or 5 |
| Mature leaflet shape | Ovate to cordate | Ovate | Oval to ovate |
| Mature leaflet apex | Broadly acuminate | Acute | Acute |
| Mature leaflet base | Cordate | Rounded | rounded to cordate |
| Mature terminal leaflet width | 8.2 cm | 7.27 cm | 6.18 cm |
| Mature terminal leaflet length | 9.7 cm | 11.47 cm | 8.28 cm |
| Mature first lateral leaflet width | 5.0 cm | 6.18 cm | 4.77 cm |
| Mature first lateral leaflet length | 7.7 cm | 9.07 cm | 6.57 cm |
| Leaflet margin | Double serrate | Double serrate | Serrate |
| Leaflet serration teeth length | 0.51 cm | 0.29 cm | 0.27 cm |
| Leaflet serration teeth width at base | 0.48 cm | 0.48 cm | 0.64 cm |
| Pubescence on floricane leaflet: upper surface | Light | Light | None |
| Pubescence on floricane leaflet: undersurface | Medium | Light | Medium |
| Floricane leaf color abaxial | RHS 139A | RHS N137A | RHS 147A |
| Floricane leaf color adaxial | RHS 139A | RHS 137C | RHS 147B |
| Petiole length | 4.2 cm | 7.07 cm | 4.43 cm |
| Petiolule length: terminal leaflet | 1.80 cm | 2.28 cm | 1.90 cm |
| Petiolule length: first distal leaflet | 0.37 cm | 0.30 cm | 0.23 cm |
| Petiolule color: abaxial | RHS 144B | RHS 145A | RHS 146C |
| Petiolule color: adaxial | RHS 144B | RHS 185A & 145A | RHS 144B |
| Stipule length | 0.99 cm | 1.36 cm | 0.25 cm |
| Stipule width | 0.25 cm | 0.12 cm | 0.04 cm |

Table 5 shows flower and flowering characteristics of the new cultivar compared with flower and flowering characteristics of the blackberry plants 'Columbia Star' and 'Black Diamond'. Flower and flowering characteristics include date 1st bloom, date full bloom, date last bloom, petal color, number flowers per cluster, number of petals per flower, flower diameter, petal length, petal width, and number of sepals per flower.

TABLE 5

| Characteristic | Zodiac | Columbia Star | Black Diamond |
|---|---|---|---|
| Date 1st bloom | 14-May | 7-May | 14-May |
| Date full bloom | 24-May | 15-May | 21-May |

TABLE 5-continued

| Characteristic | Zodiac | Columbia Star | Black Diamond |
|---|---|---|---|
| Date last bloom | 23-June | 17-June | 14-June |
| Petal color (upper and lower surfaces) | RHS NN155B | RHS 155C | RHS NN155C |
| Number flowers per cluster | 7.0 | 3.50 | 9.17 |
| Number of petals per flower | 5.5 | 5.17 | 5.33 |
| Flower diameter | 3.3 cm | 3.23 cm | 2.51 cm |
| Petal length | 1.5 cm | 1.65 cm | 1.32 cm |
| Petal width | 1.0 cm | 0.96 cm | 1.00 cm |
| Number of sepals per flower | 5.5 | 5.83 | 5.83 |
| Petal texture (upper and lower surfaces) | smooth | | |

Table 6 shows fruit and fruiting characteristics of the new cultivar compared with fruit and fruiting characteristics of the blackberry plants 'Columbia Star' and 'Black Diamond'. Fruit and fruiting characteristics include date 5% of fruit were ripe, date 50% of fruit were ripe, date 95% of fruit were ripe, weight of primary fruit, weight of secondary fruit, weight of tertiary fruit, diameter of primary fruit at equator, diameter of 2° fruit at equator, diameter of 3° fruit at equator, diameter of 1° fruit at poles: tip, diameter of 1° fruit at poles: base, diameter of 2° fruit at poles: tip, diameter of 2° fruit at poles: base, diameter of 3° fruit at poles: tip, diameter of 3° fruit at poles: base, berry length primary fruit, berry length 2° fruit, berry length 3° fruit, ratio of primary fruit length to width, shape description, uniformity of berry shape, color when full ripe, number of drupelets per fruit, drupelet weight, individual seed weight, glossiness, firmness, flavor, texture of fruit when chewed, drupelet skin resistance to abrasion, ease of separation of fruit from pedicel, machine harvestability, resistance to heat damage of fruit, berries per inflorescence—mean, berries per inflorescence range, soluble solids (%; in Brix), pH, titratable acidity (% as citric acid), and yield (actual kg*plt-1).

TABLE 6

| Characteristic | Zodiac | Columbia Star | Black Diamond |
|---|---|---|---|
| Date 5% of fruit were ripe | 25-June | 23-June | 23-June |
| Date 50% of fruit were ripe | 7-July | 30-June | 30-June |
| Date 95% of fruit were ripe | 21-July | 14-July | 14-July |
| Weight of primary fruit | 5.3 g | 7.96 g | 6.92 g |
| Weight of secondary fruit | 5.1 g | 9.68 g | 6.49 g |
| Weight of tertiary fruit | 4.9 g | 8.02 g | 6.44 g |
| Diameter of primary fruit at equator | 1.59 cm | 1.94 cm | 1.98 cm |
| Diameter of 2° fruit at equator | 1.45 cm | 1.98 cm | 1.96 cm |
| Diameter of 3° fruit at equator | 1.49 cm | 1.88 cm | 1.90 cm |
| Diameter of 1° fruit at poles: tip | 0.93 cm | 1.28 cm | 1.24 cm |
| Diameter of 1° fruit at poles: base | 1.42 cm | 1.68 cm | 1.82 cm |
| Diameter of 2° fruit at poles: tip | 0.89 cm | 1.25 cm | 1.12 cm |
| Diameter of 2° fruit at poles: base | 1.38 cm | 1.82 cm | 1.70 cm |
| Diameter of 3° fruit at poles: tip | 0.88 cm | 3.85 cm | 1.25 cm |
| Diameter of 3° fruit at poles: base | 1.46 cm | 1.73 cm | 1.76 cm |
| Berry length primary fruit | 3.34 cm | 3.83 cm | 3.19 cm |
| Berry length 2° fruit | 2.90 cm | 3.84 cm | 2.91 cm |
| Berry length 3° fruit | 2.70 cm | 3.62 cm | 2.88 cm |
| Ratio of primary fruit length to width | 2.1 | 1.98 | 1.62 |
| Shape descriprion | Conic | Conic | Conic |
| Uniformity of berry shape | Excellent | Excellent | Excellent |
| Color when full ripe | RHS 203C | RHS 203B | RHS 203B |
| Number of drupelets per fruit | 92 | 147.67 | 75.83 |
| Drupelet weight | 6.2 mg | 5.10 mg | 7.90 mg |
| Individual seed weight | 1.7 mg | 3.95 mg | 3.95 mg |

TABLE 6-continued

| Characteristic | Zodiac | Columbia Star | Black Diamond |
|---|---|---|---|
| Glossiness | Medium to high | Medium glossy to dull | Medium glossy to dull |
| Firmness | Very good | Very good | Good |
| Flavor | Very Good | Excellent | Good |
| Texture of fruit when chewed | Excellent | Very good to excellent | Very good |
| Drupelet skin resistance to abrasion | Good | Good | Good |
| Ease of separation of fruit from pedicel | Easy | Easy | Easy |
| Machine harvestability | Excellent | Excellent | Excellent |
| Resistance to heat damage of fruit | Medium to good | Medium to good | Medium to good |
| Berries per inflorescence - mean | 10.00 | 7.00 | 11.50 |
| Berries per inflorescence range | 7-14 | 5-10 | 9-14 |
| Soluble solids (%; in Brix) | 12.4 | 11.90 | 9.97 |
| pH | 3.5 | 3.20 | 3.40 |
| Titratable acidity (% as citric acid) | 14.1 | 13.77 | 12.82 |
| Yield (actual kg · plt-1) | 7.90 | 7.54 | 7.01 |

COMPARISON WITH PARENTAL AND COMMERCIAL VARIETIES

'Zodiac' differs from the female parent blackberry plant ORUS 2707-1 in that it has darker fruit color with fewer purple drupelets, well-suited firmness for machine harvest, smaller fruit size (4.7-5.3 g), similar sweetness (12.4-13.7% Brix), and similar productivity (6.3-7.6 tons/acre). By comparison, ORUS 2707-1 (unpatented) has larger fruit (7.9 g), similar sweetness (13.2% Brix), and similar productivity (7.8 tons/acre), but is softer and tends to purple, making it less well suited for machine harvest.

'Zodiac' differs from the male parent blackberry plant 'ORUS 2785-2' in that it has fruit well-suited for machine harvest, larger fruit size (4.7-5.3 g), similar sweetness (12.4-13.7% Brix), and much lower acidity (1.41 g citric acid/100 g fruit). By comparison, 'ORUS 2785-2' has very small fruit (2.6 g) due to its half-wild pedigree, with much higher tartness as a result of its higher acid content (2.54 g citric acid/100 g fruit).

'Zodiac' differs from the commercial trailing varieties 'Columbia Star' and 'Black Diamond' in that it is 7-10 days later ripening. 'Zodiac' has similar fruit quality after 7 days in refrigerated storage in plastic clam shell packaging at 4° C. to 'Columbia' and higher fruit quality than 'Black Diamond'. The 'Zodiac' fruit are smaller and glossier than 'Columbia Star' with a flavor that is slightly less aromatic and characterized more by its sweetness with good sugar/acid balance and an excellent texture that combines firm but not overly tough skin and smooth internal quality with very small seeds. The fruit quality and flavor are better than 'Black Diamond'. 'Zodiac' yields were typically similar to or slightly higher than 'Columbia' in trials held in Aurora, Oreg.

We claim:

1. A new and distinct cultivar of thornless blackberry plant named 'Zodiac', substantially as illustrated and described, characterized by its high yields of machine harvestable berries, which are uniform and conical with good firmness, skin toughness, excellent flavor, and processing quality, and combining multiple sources of genetic thornlessness.

* * * * *